United States Patent [19]

Hegendörfer

[11] Patent Number: 4,843,655
[45] Date of Patent: Jul. 4, 1989

[54] PROTECTIVE GOGGLES

[75] Inventor: Erich Hegendörfer, Cadolzburg, Fed. Rep. of Germany

[73] Assignee: Alpina Int'l Sport + Optik-Vertriebs-GmbH, Friedberg/Derching, Fed. Rep. of Germany

[21] Appl. No.: 133,721

[22] Filed: Dec. 15, 1987

[51] Int. Cl.⁴ .............................................. A61F 9/02
[52] U.S. Cl. ......................................... 2/449; 2/453; 2/439; 2/450
[58] Field of Search ................... 2/453, 449, 448, 450, 2/426, 431, 8, 439; 351/115, 41, 121

[56] References Cited

U.S. PATENT DOCUMENTS 4,527,291  7/1985  Nussbickl ................................ 2/450
4,724,546  2/1988  Cumbie, Jr. .......................... 2/453 X

FOREIGN PATENT DOCUMENTS 0149166  6/1950  Australia .................................. 2/453
83026444  7/1983  Fed. Rep. of Germany .

Primary Examiner—Peter Nerbun
Attorney, Agent, or Firm—Browdy & Neimark

[57] ABSTRACT

For the purpose of obtaining a cost-effective and esthetically pleasing design, it is provided in protective goggles, particularly sun goggles, consisting of a lens and earpieces with adjustable inclination, that the lens has flat lateral extensions in which slit-like recesses are provided through which extend parts of the ear pieces, the ear pieces being connected with each other via a lateral support extending along the upper edge of the lens, and in that a pivot bearing is formed between the lateral support and the lens.

4 Claims, 1 Drawing Sheet

PROTECTIVE GOGGLES

The invention relates to protective goggles, particularly to sun goggles, having a lens and ear pieces with adjustable inclination.

BACKGROUND OF THE INVENTION

Such protective goggles are known, e.g. as protective work goggles, from German Utility Model DE-GM 83 02 644. The known design satisfies exact professional demands.

In contrast thereto and especially in the area of sun glasses, there exists a demand for inclinable ear pieces on the one hand while, on the other, construction effort is to be kept as low as possible in view of manufacturing costs. Furthermore, the structure should be such that it results in a pleasing esthetic design.

SUMMARY OF THE INVENTION

Based on the foregoing, it is an object of the invention to design protective goggles of the type referred to above, such that the adjustment of the inclination can be easily accomplished while keeping production cost-effective and the design pleasing.

This object is attained by providing the lens with lateral flat extensions and providing slit-like recesses in the extensions through which parts of the ear pieces extend. The ear pieces are connected with each other by means of a lateral support extending along the area of the upper edge of the lens, and a pivot bearing is provided between the lateral support and the lens.

Because of this type of construction, the extensions can be formed in one piece together with the lens and the guide recesses in the extensions, so that no additional, perhaps separately-manufactured parts are required for the inclination adjustment devices.

A further embodiment can provide a ribbing in the slit-like recesses, so that a definite fixation in a position of a predetermined angle is possible.

The ear pieces and the lateral support are advantageously formed in one piece. Because of this embodiment the entire pair of goggles can be made from only one extruded parts, i.e. the ear pieces and lateral support on the one hand and the lens with the extensions on the other. This additionally results in a particularly pleasing design.

It is also in line with the concept of the invention, that is, using as few parts as possible, to form the pivot bearing between the lateral support and the lens by pivot bearing elements which have been extruded as one piece with the lateral support or, respectively, with the lens. For example, the pivot bearing can be realized by an extension which has been extruded on the lateral support and extends through a recess in the lens.

Further characteristics, advantages and details of the invention can be seen in the ensuing description of a preferred embodiment taken in conjunction with the drawings.

DETAILED DESCRIPTION OF THE PREFERRED EMBODIMENT

Figure 1:
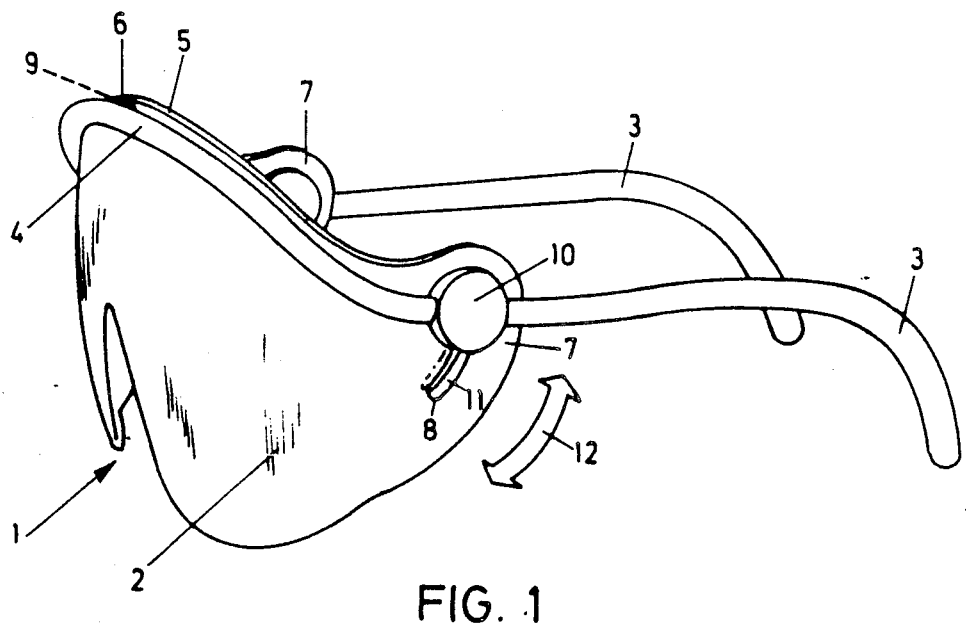
FIG. 1 is a schematic perspective view of a preferred embodiment of the protective goggles according to the invention.

The protective goggles 1 shown in the drawings are in the form of sun goggles. They include a one-piece lens 2, two ear pieces 3 made in the customary way and representing a one-piece design, and a lateral support 4, connected with the latter in one piece and extending along the upper edge 5 on the outside of the lens 3.

Figure 2:
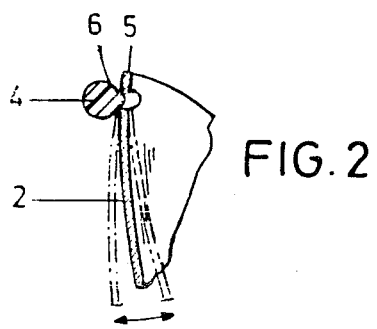
FIG. 2 is a partial section across the pivot bearing.

The lateral support 4 is connected with the lens 2 via a pivot bearing 6 shown in FIG. 2. The pivot bearing 6 is realized in this example by means of an inwardly protruding extension extruded on the lateral support 4, which snaps into a recess of the lens 2 such that the lateral support and the lens are pivotable in relation to each other.

The lens 2 has an extension 7 in which arcuate slits 8 are formed, extending around the axis 9 of the pivot bearing 6.

A guide element 10 is formed in one piece with the ear pieces 3 on their forward ends and a tang-shaped extension of the guide element 10, not shown in the drawing, engages the slit 8.

A defined inclination adjustment around the pivot axis 9 is made possible by the pivot bearing 6 on the one hand and the guide element 10 or, respectively, the slit 8 on the other. Ribbed protrusions, not shown in detail, can be formed on the inner front sections 11 of the slit 8, which make possible the fixation of the ear pieces 3 in a definite end position after an adjustment of the inclination in the direction of the arrow 12.

The foregoing description of the specific embodiment(s) will so fully reveal the general nature of the invention that others can, by applying current knowledge, readily modify and/or adapt for various applications such specific embodiment(s) without departing from the generic concept, and therefore, such adaptations and modifications should and are intended to be comprehended within the meaning and range of equivalents of the disclosed embodiment(s). It is to be understood that the praseology or terminology employed herein is for the purpose of description and not of limitation.

What is claimed is:

1. Protective goggles comprising
   a lens with a pair of flat lateral extensions,
   a pair of ear pieces, each having a front thereof extending past a respective one of said lateral extensions of said lens,
   a lateral support extending along an upper edge of said lens and being connected at two ends to said ear pieces in the vicinity of said fronts thereof, and
   adjusting means for providing adjustable inclination between said lens and ear pieces, comprising slit-like recesses formed in said flat lateral extensions of said lens, guide elements arranged at said ear pieces extending from said fronts thereof through said slit-like recesses,
   pivot means provided between said lateral support and lens, wherein said ear pieces and said lateral support are formed in one piece and wherein said pivot means comprises a bearing element extruded in one piece with a predetermined one of said lateral support and lens.

2. The goggles of claim 1, wherein ribbing is provided on said flat lateral extensions of said lens, along said slit-like recesses, to define respective positions of adjustment of said inclination.

3. The goggles of claim 1, wherein said pivot means comprises a bearing element extruded in one piece with both said lateral support and lens.

4. The protective goggles of claim 1, said lens, ear pieces, lateral support and adjusting means consisting of only two pieces, each said piece having been formed by extrusion.

* * * * *